US006583206B2

(12) United States Patent
Zhao

(10) Patent No.: US 6,583,206 B2
(45) Date of Patent: *Jun. 24, 2003

(54) SATURATED [2.2.2] DICARBOXYLATE SALT THERMOPLASTIC NUCLEATORS AND THERMOPLASTIC COMPOSITIONS THEREOF

(75) Inventor: Xiaodong Edward Zhao, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 233 days.

This patent is subject to a terminal disclaimer.

(21) Appl. No.: 09/874,858

(22) Filed: Jun. 5, 2001

(65) Prior Publication Data

US 2003/0004242 A1 Jan. 2, 2003

(51) Int. Cl.[7] .............................. C08J 3/00; C07C 61/12
(52) U.S. Cl. ..................... 524/242; 524/285; 524/396; 524/399; 524/378; 524/381; 524/382; 524/398; 524/400; 556/115; 556/132; 556/170; 562/502
(58) Field of Search ................................ 524/285, 396, 524/242, 399, 378, 381, 382, 398, 400; 556/115, 132, 170; 562/502

(56) References Cited

U.S. PATENT DOCUMENTS

| 5,922,793 A | 7/1999 | Amos et al. ................. 524/159 |
| 5,929,146 A | 7/1999 | Amos et al. ................... 524/89 |
| 5,981,636 A | 11/1999 | Amos et al. ................. 524/108 |
| 6,096,811 A | 8/2000 | Amos et al. ................... 524/89 |

*Primary Examiner*—Peter D. Mulcahy
(74) *Attorney, Agent, or Firm*—Terry T. Moyer; William S. Parks

(57) ABSTRACT

Compounds of and compositions comprising specific salts of saturated [2.2.2] dicarboxylate in order to provide highly desirable properties within thermoplastic (e.g., polyolefin) articles are provided. The inventive salts and derivatives thereof are useful as nucleating and/or clarifying agents for such thermoplastics, are easy to produce and handle, and relatively inexpensive to manufacture. Such compounds induce high peak crystallization and improved stiffness within thermoplastics. Also, thermoplastic compositions comprising such novel nucleating agents exhibit improved heat distortion properties and clarity levels in comparison with the closest unsaturated salt nucleating agents. Thermoplastic additive compositions and methods of producing thermoplastics with such compounds are also contemplated within this invention.

25 Claims, No Drawings

SATURATED [2.2.2] DICARBOXYLATE SALT THERMOPLASTIC NUCLEATORS AND THERMOPLASTIC COMPOSITIONS THEREOF

FIELD OF THE INVENTION

This invention relates to compounds and compositions comprising specific salts of saturated [2.2.2] dicarboxylate in order to provide highly desirable properties within thermoplastic (e.g., polyolefin) articles. The inventive salts and derivatives thereof are useful as nucleating and/or clarifying agents for such thermoplastics, are easy to produce and handle, and relatively inexpensive to manufacture. Such compounds induce high peak crystallization and improved stiffness within thermoplastics. Also, thermoplastic compositions comprising such novel nucleating agents exhibit improved heat distortion properties and clarity levels in comparison with the closest unsaturated salt nucleating agents. Thermoplastic additive compositions and methods of producing thermoplastics with such compounds are also contemplated within this invention.

BACKGROUND OF THE PRIOR ART

All U.S. patents cited below are herein entirely incorporated by reference.

As used herein, the term "thermoplastic" is intended to mean a polymeric material that will melt upon exposure to sufficient heat but will retain its solidified state, but not prior shape without use of a mold or like article, upon sufficient cooling. Specifically, as well, such a term is intended solely to encompass polymers meeting such a broad definition that also exhibit either crystalline or semi-crystalline morphology upon cooling after melt-formation. Particular types of polymers contemplated within such a definition include, without limitation, polyolefin (such as polyethylene, polypropylene, polybutylene, and any combination thereof), polyamides (such as nylon), polyurethanes, polyesters (such as polyethylene terephthalate), and the like (as well as any combinations thereof).

Thermoplastics have been utilized in a variety of end-use applications, including storage Containers, medical devices, food packages, plastic tubes and pipes, shelving units, and the like. Such base compositions, however, must exhibit certain physical characteristics in order to permit widespread use. Specifically within polyolefin, for example, uniformity in arrangement of crystals upon crystallization is a necessity to provide an effective, durable, and versatile polyolefin article. In order to achieve such desirable physical properties, it has been known that certain compounds and compositions provide nucleation sites for polyolefin crystal growth during molding or fabrication. Generally, compositions containing such nucleating compounds crystallize at a much faster rate than un-nucleated polyolefin. Such crystallization at higher temperatures results in reduced fabrication cycle times and a variety of improvements in physical properties, such as, as one example, stiffness.

Such compounds and compositions that provide faster and or higher polymer crystallization temperatures are thus popularly known as nucleators. Such compounds are, as their name suggests, utilized to provide nucleation sites for crystal growth during cooling of a thermoplastic molten formulation. Generally, the presence of such nucleation sites results in a larger number of smaller crystals. As a result of the smaller crystals formed therein, clarification of the target thermoplastic may also be achieved, although excellent clarity is not always a result. The more uniform, and preferably smaller, the crystal size, the less light is scattered. In such a manner, the clarity of the thermoplastic article itself can be improved. Thus, thermoplastic nucleator compounds are very important to the thermoplastic industry in order to provide enhanced clarity, physical properties and/or faster processing.

As an example of one type of nucleator, dibenzylidene sorbitol derivative compounds are typical nucleator compounds, particularly for polypropylene end products. Compounds such as 1,3-O-2,4-bis(3,4-dimethylbenzylidene) sorbitol, available from Milliken Chemical under the trade name Millad® 3988, provide excellent nucleation characteristics for target polypropylenes and other polyolefin. Other well known compounds include sodium benzoate, sodium 2,2'-methylene-bis-(4,6-di-tert-butylphenyl) phosphate (from Asahi Denk Kogyo K.K., known as NA-11), aluminum bis[2,2'-methylene-bis-(4,6-di-tert-butylphenyl)phosphate] (also from Asahi Denka Kogyo K.K., known as NA-21), talc, and the like. Such compounds all impart high polyolefin crystallization temperatures; however, each also exhibits its own drawback for large-scale industrial applications.

Other acetals of sorbitol and xylitol are typical nucleators for polyolefin and other thermoplastics as well. Dibenzylidene sorbitol (DBS) was first disclosed in U.S. Pat. No. 4,016,118 by Hamada, et al. as effective nucleating and clarifying agents for polyolefin. Since then, large numbers of acetals of sorbitol and xylitol have been disclosed. Representative references of such other compounds include Mahaffey, Jr., U.S. Pat. No. 4,371,645 [di-acetals of sorbitol having at least one chlorine or bromine substituent].

As noted above, another example of the effective nucleating agents are the metal salts of organic acids. Wijga in U.S. Pat. Nos. 3,207,735, 3,207,736, and 3,207,738, and Wales in U.S. Pat. Nos. 3,207,737 and 3,207,739, suggest that aliphatic, cycloaliphatic, and aromatic carboxylic, dicarboxylic or higher polycarboxylic acids, and corresponding anhydrides and metal salts, are effective nucleating agents for polyolefin. They further state that benzoic acid type compounds, in particular sodium benzoate, are the best nucleating agents for their target polyolefin.

Another class of nucleating agents was suggested by Nakahara, et al. in U.S. Pat. No. 4,463,113, in which cyclic bis-phenol phosphates was disclosed as nucleating and clarifying agents for polyolefin resins. Kimura, et al. then suggests in U.S. Pat. No. 5,342,868 that the addition of an alkali metal carboxylate to basic polyvalent metal salt of cyclic organophosphoric ester can further improve the clarification effects of such additives. Compounds that are based upon this technologies are marketed under the trade name NA-11 and NA-21.

Furthermore, a certain class of bicyclic compounds, such as bicyclic dicarboxylic acid and salts, have been taught as polyolefin nucleating agents as well within Patent Cooperation Treaty Application WO 98/29494, 98/29495 and 98/29496, all assigned to Minnesota Mining and Manufacturing. The best working examples of this technology is embodied in disodium bicyclo[2.2.1]heptene dicarboxylate, disodium bicyclo[2.2.2]octene dicarboxylated and camphanic acid. Formulations with such compounds are also contemplated within the inventions.

The efficacy of the nucleating agents are typically measured by the peak crystallization temperature of the polymer compositions containing such nucleating agents. A high polymer peak crystallization is indicative of high nucleation efficacy, which generally translates into fast processing cycle time and more desirable physical properties, such as stiffness/impact balance etc., for the fabricated parts.

It is also very desirable that the nucleating agents induce improved clarity in the fabricated parts. DBS based Nucleating agents are known to provide excellent clarity in polypropylene articles. For example, 3,4-dimethyl DBS, marketed under the trade name Millad 3988 is an exceptional clarifier. However, DBS based nucleating agents generally suffer from higher level of migration and certain ones [for example bis(p-methyl benzylidene) sorbitol)] from highly undesirable taste and odor transfer. Site nucleators, which are loosely defined as nucleating agents that are not soluble in molten polyolefin, provide better performance in migration, taste and odor transfer. Typically site nucleators include Na-11, sodium benzoate and alike. Site nucleators generally do not afford sufficient clarification effect in polyolefin articles. Therefore, there is a long felt need for a site nucleating agents with improved clarification property.

Depending upon the application, polyolefin articles can be subjected to elevated temperature and mechanical stress for a long period of time. Such applications might include food and beverage containers, automotive parts, certain outdoor application. Dimensional stability at elevated temperature under stress is very important for these applications. Thus, improved dimensional stability at higher temperature is of significant economic value. Dimensional stability at higher temperature are typically measured by heat distortion temperature, which is defined as the temperature at which an arbitrary deformation occurs when the test specimens are subjected to an arbitrary level of stress. Nucleating agents are known to increase the heat distortion temperature of polyolefin. Nucleating agents that induce provide improved heat distortion temperatures are thus highly desirable and necessary within certain polyolefin articles. To date, no [2.2.2]dicarboxylate salts have been taught or fairly suggested within the prior art that induce good peak crystallization temperatures, clarity, and high heat distortion temperatures simultaneously within target thermoplastics.

OBJECTS OF THE INVENTION

Therefore, an object of the invention is to provide a nucleator compound and compositions thereof of the [2.2.2] dicarboxylate salt type that induces excellent high peak crystallization temperatures to polypropylene articles and formulations and also provides improved clarity and heat distortion temperatures in the same articles and formulations. Additionally, it is an object of this invention to provide a nucleator compound or composition that may be used in various polyolefin media for use in myriad end-uses.

Accordingly, this invention encompasses metal or organic salts of saturated [2.2.2]dicarboxylates, preferably bicyclic dicarboxylates, and most preferably of compounds conforming to Formula (I)

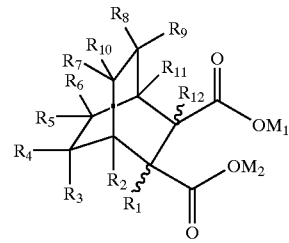

wherein $M_1$ and $M_2$ are the same or different, or $M_1$ and $M_2$ are combined to from a single moiety, and are independently selected from the group consisting of metal or organic cations, and $R_1$, $R_2$, $R_3$, $R_4$, $R_5$, $R_6$, $R_7$, $R_8$, $R_9$, $R_{10}$, $R_{11}$, and $R_{12}$ are individually selected from the group consisting of hydrogen, $C_1$–$C_9$ alkyl, hydroxy, $C_1$–$C_9$ alkoxy, $C_1$–$C_9$ alkyleneoxy, amine, $C_1$–$C_9$ alkylamine, halogen, phenyl, alkylphenyl, and geminal and vicinal $C_1$–$C_9$ carbocyclic. Polyolefin articles and additive compositions for polyolefin formulations comprising at least one of such compounds are also encompassed within this invention.

DETAILED DESCRIPTION OF THE INVENTION

As noted above, in order to develop a proper polyolefin nucleator compound or composition for industrial applications, a number of important criteria needed to be met. The inventive nucleating agents meet all of these important requirements very well. For instance, as discussed in greater detail below, these inventive salts provide high peak crystallization temperatures in a variety of polyolefin formulations, particularly within random copolymer polypropylene (hereinafter RCP) and homopolymer polypropylene (hereinafter HP). As a result, such inventive salts provide excellent mechanical properties for polyolefin articles without the need for extra fillers and rigidifying additives, and desirable processing characteristics such as improved (shorter) cycle time. The salts also show much improved clarity comparing to prior art. Lastly, such inventive salts provide improved heat distortion temperature when comparing to the closest prior art.

Such properties are highly unexpected and unpredictable, particularly in view of the closest prior art, the WO 98/29494 reference discloses nucleation and clarification additives for polyolefin articles including unsaturated[2.2.2] dicarboxylate salts; however, there is no exemplification of a saturated dicarboxylate salt of this type. The closest embodiment within that art is identified as disodium bicyclo[2.2.2]octene dicarboxylate. After intensive investigations, it has been determined that, quite unexpectedly, as discussed below in greater detail, the hydrogenation of such compounds provides significant improved nucleation efficacy and other properties for the target and inventive thermoplastic (e.g., polyolefin, and the like) compositions. It has now been found that the saturation of Diels-Alder reaction products to form dicarboxylate salts, and in particular, without intending to limit the scope of the invention, saturated bicyclic dicarboxylate salts, provide unforeseen benefits for polyolefin nucleation processes.

As indicated in Table 1, below, the haze provided target polyolefin articles with these inventive saturated compounds are from about 4 units (4%) lower than that for the related unsaturated compounds. Such improvements are simply unexpected and are unpredictable from any known empirical or theoretical considerations. Furthermore, significant improvements in heat distortion temperature of the saturated compounds were also unexpectedly observed as shown in Table 2, below. Such unpredictable improvements are of great practical significance as discussed before.

The inventive salts are thus added within the target polyolefin in an amount from about 50 ppm to about 20,000 pm by weight in order to provide the aforementioned beneficial characteristics, most preferably from about 200 to about 4000 ppm. Higher levels, e.g., 50% or more by weight, may also be used in a masterbatch formulation. Optional additives within the inventive salt-containing composition, or within the final polyolefin article made therewith, may include plasticizers, antistatic agents, stabilizers, ultraviolet absorbers, and other similar standard polyolefin thermoplastic additives. Other additives may also be present within this composition, most notably antioxidants, antistatic compounds, perfumes, chlorine scavengers, and the like. Such additives, and others not listed, are well known to those skilled in the art.

The term polyolefin or polyolefin resin is intended to encompass any materials comprised of at least one polyolefin compound. Preferred examples include isotactic and syndiotactic polypropylene, polyethylene, poly(4-methyl) pentene, polybutylene, and any blends or copolymers thereof, whether high or low density in composition. The polyolefin polymers of the present invention may include aliphatic polyolefin and copolymers made from at least one aliphatic olefin and one or more ethylenically unsaturated co-monomers. Generally, the co-monomers, if present, will be provided in a minor amount, e.g., about 10 percent or less or even about 5 percent or less, based upon the weight of the polyolefin (e.g. random copolymer polypropylene), but copolymers containing up to 25% or more of the co-monomer (e.g., impact copolymers) are also envisaged. Other polymers or rubber (such as EPDM or EPR) may also be compounded with the polyolefin to obtain the aforementioned characteristics. Such co-monomers may serve to assist in clarity improvement of the polyolefin, or they may function to improve other properties of the polymer. Other examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as, without limitation, polyethylene, linear low density polyethylene, isotactic polypropylene, syndiotactic polypropylene, crystalline ethylenepropylene copolymer, poly(1-butene), polymethylpentene, 1-hexene, 1-octene, and vinyl cyclohexane. The polyolefin of the present invention may be described as basically linear, regular polymers that may optionally contain side chains such as are found, for instance, in conventional low density polyethylene.

Although polyolefin are preferred, the nucleating agents of the present invention are not restricted to polyolefin, and may also give beneficial nucleation properties to polyesters such as polyethylene terephthalate (PET), polybutylene terephthalate (PBT), and polyethylene naphthalate (PEN), as well as polyamides such as Nylon 6, Nylon 6,6, and others. Generally, any thermoplastic composition having some crystalline content may be improved with the nucleating agents of the present invention.

The compositions of the present invention may be obtained by adding the inventive saturated bicyclic dicarboxylic salt (or combination of salts or composition comprising such salts) to the thermoplastic polymer or copolymer and merely mixing the resultant composition by any suitable means. Alternatively, a concentrate containing as much as about 20 percent by weight of the inventive saturated [2.2.2] salt in a polyolefin masterbatch comprising the required acid scavenger may be prepared and be subsequently mixed with the target resin. Furthermore, the inventive compositions (with other additives potentially) may be present in any type of standard thermoplastic (e.g., polyolefin, most preferably) additive form, including, without limitation, powder, prill, agglomerate, liquid suspension, and the like, particularly comprising dispersion aids such as polyolefin (e.g., polyethylene) waxes, stearate esters of glycerin, montan waxes, mineral oil, and the like. Basically, any form may be exhibited by such a combination or composition including such combination made from blending, agglomeration, compaction, and/or extrusion.

The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

PREFERRED EMBODIMENTS OF THE INVENTION

Examples of particularly preferred fluid dispersions within the scope of the present invention are presented below.

Production of Inventive Salts

EXAMPLE 1

Disodium bicyclo[2.2.2]octane-2,3-dicarboxylate

To a solution of disodium bicyclo[2.2.1]oct-5-en-2,3-dicarboxylate (10.0 g, from example 3) in water (100 g) was added 0.5 g palladium on activated carbon (5 wt %). The mixture was transferred into a Parr reactor and was subjected to hydrogenation (50 psi, room temperature) for 8 hours. The activated carbon was filtered out. Water is removed in vacuo at 75° C. The resulting product was dried and milled (m.p>300° C.).

EXAMPLE 2 (COMPARATIVE)

Disodium bicyclo[2.2.2]oct-5-en-2,3-dicarboxylate

To a solution of maleic anhydride (10.30 g) in toluene (100 ml) was added 1,3-cyclohexadiene (8.41 g). The mixture was refluxed for 3 hours. After cooling to 25° C., the solvent was evaporated at reduced pressure. The solid was recrystallized from EtOAC/hexane to yield bicyclo[2.2.2] oct-en-2,3-dicarboxylic anhydride as colorless crystals.

To a suspension of endo-bicyclo[2.2.1]oct-5-en-2,3-dicarboxylic anhydride (17.8 g, 0.1 mol) in water (100 g) was added sodium hydroxide (8.0 g, 0.2 mol) at room temperature. The mixture was then stirred at 80° C. for 2 hour. A clear, homogeneous solution was obtained. Water was removed in vacuo at 75° C. and the resulting white crystalline product was dried and milled (m.p.>300° C.).

Other salts of lithium, rubidium, potassium, strontium, barium, and magnesium dicarboxylate salts were prepared in like manners.

Nucleation Efficacy Test

Thermoplastic compositions (plaques) were produced comprising the additives from the Examples above and sample homopolymer polypropylene (HP) resin plaques, produced dry blended in a Welex mixer at ~2000 rpm, extruded through a single screw extruder at 400–450° F., and pelletized. Accordingly, one kilogram batches of target polypropylene were produced in accordance with the following table:

| HOMOPOLYMER POLYPROPYLENE COMPOSITION TABLE | |
| --- | --- |
| Component | Amount |
| Polypropylene homopolymer (Himont Profax ® 6301) | 1000 g |
| Irganox ® 1010, Primary Antioxidant (from Ciba) | 500 ppm |
| Irgafos ® 168, Secondary Antioxidant (from Ciba) | 1000 ppm |
| DHT-4A, Acid Scavenger | as noted |
| Calcium Stearate, Acid Scavenger | as noted |
| Inventive Nucleator | as noted |

The base HP [having a density of about 0.9 g/cc, a melt flow of about 12 g/10 min, a Rockwell Hardness (R scale) of about 90, a tensile strength of about 4,931 psi, an elongation at yield of about 10%, a flexural modulus of about 203 ksi, an Izod impact strength of about 0.67 ft-lb/in, and a deflection temperature at 0.46 mPa of about 93° C., as well as an expected isotacticity of between about 96 and 99% through xylene solubles analysis] and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The molder was set at a temperature anywhere between 190 and 260° C., with a range of 190 to 240° C. preferred, most preferably from about 200 to 230° C. The plaques had dimensions of about 51 mm×76 mm×1.27 mm, and the mold had a mirror finish which was transferred to the individual plaques. The mold cooling circulating water was controlled at a temperature of about 25° C.

Testing for nucleating effects and other important criteria were accomplished through the formation of plaques of clarified polypropylene thermoplastic resin. These plaques were formed through the process outlined above with the specific compositions listed above in the above Table.

These plaque formulations are, of course, merely preferred embodiments of the inventive article and method and are not intended to limit the scope of this invention. The resultant plaques were then tested for peak crystallization temperatures (by Differential Scanning Calorimetry). Crystallization is important in order to determine the time needed to form a solid article from the molten polyolefin composition. Generally, a polyolefin such as polypropylene has a crystallization temperature of about 110° C. at a cooling rate of 20° C./min. In order to reduce the amount of time needed to form the final product, as well as to provide the most effective nucleation for the polyolefin, the best nucleator compound added will invariably also provide the highest crystallization temperature for the final polyolefin product. The nucleation composition efficacy, particular polymer peak crystallization temperature ($T_c$), was evaluated by using a modified differential scanning procedure based upon the test protocol ASTM D3417-99 wherein the heating and cooling rates utilized have been altered to 20° C./minute each. Thus, to measure the peak crystallization temperatures of the samples, the specific polypropylene compositions were heated from 60° C. to 220° C. at a rate of 20° C. per minute to produce molten formulations and held at the peak temperature for 2 minutes. At that time, the temperature was then lowered at a rate of 20° C. per minute until it reached the starting temperature of 60° C. for each individual sample. The important crystallization temperatures were thus measured as the peak maxima during the individual crystallization exotherms for each sample. After allowing the plaques to age for 24 hours at room temperature, haze values were measured according to ASTM Standard Test Method D1003-61 "Standard Test Method for Haze and Luminous Transmittance of Transparent Plastics" using a BYK Gardner Hazegard Plus.

The following Table lists the peak crystallization temperatures and haze results for the sample plaques prepared with the additives noted above (with certain acid scavengers and levels thereof as well as levels of nucleating agent used therein specified for each sample; Samples 5–10, below included 2500 ppm each of the nucleating agent):

| EXPERIMENTAL TABLE 1 Performance of Bicyclic Nucleators in Polypropylene Homopolymer | | | |
| --- | --- | --- | --- |
| Sample # | Nucleator Conc. (ppm) | Peak $T_c$ (° C.) | Haze (%) |
| 1 | Example 1 (1000 ppm)$^a$ | 122.5 | 35 |
| 2 | Example 1 (2500 ppm)$^b$ | 124.1 | 30 |
| 3 | Example 2 (1000 ppm)$^a$ | 122.4 | 39 |
| 4 | Example 2 (2500 ppm)$^b$ | 123.7 | 35 |

The data show that inventive nucleating agents of Example 1 exhibit improved clarity (lower haze) and simultaneous high polymer crystallization temperature comparing to the nucleating agent in example 2.

Another important test for nucleation efficacy is the heat distortion temperature of the nucleated thermoplastic. Heat distortion is defined as the temperature at which an arbitrary deformation occurs within the thermoplastic when the sample thermopalstic is subjected to an arbitrary level of stress. Data from this test may be used to predict the behavior of plastic materials at elevated temperatures. In a practical sense, a higher heat distortion is indicative of higher dimensional stability at elevated temperature, and therefore, of significant economic value.

Nucleating agents are known to increase the heat distortion temperature of polyolefin. The degree of enhancement is an indication of nucleation efficacy. The heat distortion measurement was conducted on a Ceast® HDT3 using ASTM Method D648-98c "Standard Test Method for Deflection Temperature of Plastics Under Flexural Load in the Edgewise Position". The test specimens were loaded to a fiber stress of 1.82 mPa. The test specimens (plaques) were approximately 127 mm in length, 12.7 mm in depth, and 3.2 mm in width and were made from the same formulations and by the same process as for the Polypropylene Composition listed above. The test data are summarized in the Table below:

EXPERIMENTAL TABLE 2
Heat Distortion Temperature in Homopolymer

| Sample # (from Experimental Table 1) | Loading (ppm) | HDT ( C) |
|---|---|---|
| Control | ----- | 91.8 |
| Example 2 (Comparative) | 1000 | 106.2 |
| Example 2 (Comparative) | 2500 | 111.3 |
| Example 1 | 1000 | 110.9 |
| Example 1 | 2500 | 113.2 |

The data show that the inventive nucleating agent induces improved heat distortion temperature as compared with the unsaturated nucleating agent of Example 2. This result is unexpected and of significant value to the thermoplastic compounder.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A compound conforming to the structure of Formula (I)

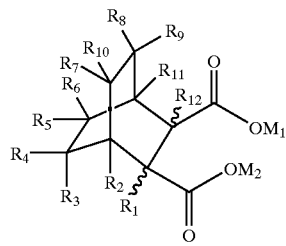

(I)

wherein $M_1$ and $M_2$ are the same or different and are independently selected from the group consisting of metal or organic cations, or wherein $M_1$ and $M_2$ are combined to form a single cation, and $R_1$, $R_2$, $R_3$, $R_4$, $R_5$, $R_6$, $R_7$, $R_8$, $R_9$, $R_{10}$, $R_{11}$, and $R_{12}$ are individually selected from the group consisting of hydrogen, $C_1$–$C_9$ alkyl, hydroxy, $C_1$–$C_9$ alkoxy, $C_1$–$C_9$ alkyleneoxy, amine, $C_1$–$C_9$ alkylamine, halogen, phenyl, alkylphenyl, and geminal or vicinal carbocyclic having up to nine carbon atoms.

2. The compound of claim 1 wherein said metal or organic cation is a metal cation selected from the group consisting of Group I and Group II metal ions.

3. The compound of claim 2 wherein said metal cation is selected from the group consisting of sodium, potassium, calcium, lithium, rubidium, barium, magnesium, and strontium, silver, zinc, aluminum.

4. The compound of claim 3 wherein said metal cation is sodium or calcium.

5. A thermoplastic article comprising at least one compound as defined in claim 1.

6. A thermoplastic article comprising at least one compound as defined in claim 2.

7. A thermoplastic article comprising at least one compound as defined in claim 3.

8. A thermoplastic article comprising at least one compound as defined in claim 4.

9. The thermoplastic article of claim 5 comprising a polyolefin.

10. The thermoplastic article of claim 6 comprising a polyolefin.

11. The thermoplastic article of claim 7 comprising a polyolefin.

12. The thermoplastic article of claim 8 comprising a polyolefin.

13. The thermoplastic article of claim 5 comprising a polyester.

14. The thermoplastic article of claim 6 comprising a polyester.

15. The thermoplastic article of claim 7 comprising a polyester.

16. The thermoplastic article of claim 8 comprising a polyester.

17. A polymer additive composition comprising at least one compound defined in claim 1, wherein said additive composition is present in a form selected from the group consisting of a powder, a pellet, or a liquid, and wherein said composition also comprises at least one polymer, and, optionally, at least one compound selected from the group consisting of plasticizers, acid scavengers, antioxidants, antimicrobials, flame retardants, light stabilizers, antistatic agents, colorants, pigments, and any combination thereof.

18. A polymer additive composition comprising at least one compound defined in claim 2, wherein said additive composition is present in a form selected from the group consisting of a powder, a pellet, or a liquid, and wherein said composition also comprises at least one polymer, and, optionally, at least one compound selected from the group consisting of plasticizers, acid scavengers, antimicrobials, antioxidants, flame retardants, light stabilizers, antistatic agents, colorants, pigments, and any combination thereof.

19. A polymer additive composition comprising at least one compound defined in claim 3, wherein said additive composition is present in a form selected from the group consisting of a powder, a pellet, or a liquid, and wherein said composition also comprises at least one polymer, and, optionally, at least one compound selected from the group consisting of plasticizers, acid scavengers, antimicrobials, antioxidants, flame retardants, light stabilizers, antistatic agents, colorants, pigments, and any combination thereof.

20. A polymer additive composition comprising at least one compound defined in claim 4, wherein said additive composition is present in a form selected from the group consisting of a powder, a pellet, or a liquid, and wherein said composition also comprises at least one polymer, and, optionally, at least one compound selected from the group consisting of plasticizers, acid scavengers, antimicrobials, antioxidants, flame retardants, light stabilizers, antistatic agents, colorants, pigments, and any combination thereof.

21. A thermoplastic article comprising at least one saturated bicylic dicarboxylate salt compound.

22. The thermoplastic article of claim 21 wherein said thermoplastic comprises a polyolefin.

23. The thermoplastic article of claim 21 wherein said thermoplastic comprises a polyester.

24. A method of nucleating a polyolefin comprising the steps of:

(a) providing a nucleator composition comprising at least 100 ppm of the compound of claim 1;

(a) providing a polyolefin formulation;

(b) mixing said composition of step "a" with the polyolefin of step "b";

(c) melting said resultant mixture of step "c"; and (d) allowing said molten mixture of step "d" to cool.

25. A method of nucleating a polyolefin comprising the steps of:

(e) providing a nucleator composition comprising the polyolefin additive composition of claim 17;

(a) providing a polyolefin formulation;

(f) mixing said composition of step "a" with the polyolefin of step "b";

(g) melting said resultant mixture of step "c"; and (h) allowing said molten mixture of step "d" to cool.

* * * * *